(12) United States Patent (10) Patent No.: US 6,887,208 B2
Kushnir et al. (45) Date of Patent: May 3, 2005

(54) METHOD AND SYSTEM FOR ANALYZING RESPIRATORY TRACT SOUNDS

(75) Inventors: Igal Kushnir, Pardes Hana (IL); Meir Botbol, Pardes Hana (IL)

(73) Assignee: Deepbreeze Ltd., Caesarea (IL)

( * ) Notice: Subject to any disclaimer, the term of this patent is extended or adjusted under 35 U.S.C. 154(b) by 82 days.

(21) Appl. No.: 10/338,742

(22) Filed: Jan. 9, 2003

(65) Prior Publication Data

US 2003/0139679 A1 Jul. 24, 2003

Related U.S. Application Data

(63) Continuation-in-part of application No. 10/041,494, filed on Jan. 10, 2002, now abandoned.

(51) Int. Cl.⁷ ................................................ A61B 5/08
(52) U.S. Cl. ...................................... 600/529; 600/586
(58) Field of Search ............................... 600/300, 301, 600/407–411, 421, 437, 438, 450, 481, 493, 528–543, 586, 587; 381/56, 71.1–71.14, 124; 73/570; 702/19

(56) References Cited

U.S. PATENT DOCUMENTS

| | | | |
|---|---|---|---|
| 3,604,852 A | 9/1971 | Weintraub | |
| 4,289,142 A | 9/1981 | Kearns | |
| 4,387,722 A | 6/1983 | Kearns | |
| 4,777,961 A | 10/1988 | Saltzman | |
| 4,833,625 A | 5/1989 | Fisher et al. | |
| 5,010,889 A | 4/1991 | Bredesen et al. | |
| 5,058,600 A | 10/1991 | Schechter et al. | |
| 5,213,108 A | 5/1993 | Bredesen et al. | |
| 5,218,969 A | 6/1993 | Bredesen et al. | |
| 5,309,922 A | 5/1994 | Schechter et al. | |
| 5,492,125 A | 2/1996 | Kim et al. | |
| 5,526,442 A | 6/1996 | Baba et al. | |
| 5,774,558 A | 6/1998 | Drucker | |
| 5,844,997 A | 12/1998 | Murphy | |
| 5,957,866 A | 9/1999 | Shapiro et al. | |
| 6,135,960 A | 10/2000 | Holmberg | |
| 6,139,505 A * | 10/2000 | Murphy | 600/532 |
| 6,140,565 A | 10/2000 | Yamauchi et al. | |
| 6,168,568 B1 * | 1/2001 | Gavriely | 600/529 |
| 6,234,963 B1 | 5/2001 | Blike et al. | |
| 6,236,886 B1 | 5/2001 | Cherepenin et al. | |
| 6,341,229 B1 | 1/2002 | Akiva | |
| 6,381,351 B1 | 4/2002 | Powell | |
| 6,396,931 B1 | 5/2002 | Malilay | |
| 2002/0028006 A1 | 3/2002 | Novak et al. | |
| 2002/0049375 A1 | 4/2002 | Strommer et al. | |
| 2002/0052559 A1 | 5/2002 | Watrous | |
| 2002/0058889 A1 | 5/2002 | Lee | |

FOREIGN PATENT DOCUMENTS

| | | |
|---|---|---|
| GB | 2 225 948 A | 6/1990 |
| JP | 4-82538 | 3/1992 |
| RU | 993917 | 6/1981 |
| WO | WO 97/29687 | 8/1997 |

OTHER PUBLICATIONS

"Acoustic Imaging of the Human Chest", Martin Kompis, et al., CHEST—Oct. 2001 pp. 1309–1321.

* cited by examiner

Primary Examiner—Eric F. Winakur
Assistant Examiner—Patricia C. Mallari
(74) Attorney, Agent, or Firm—Birch, Stewart, Kolasch & Birch, LLP

(57) ABSTRACT

A method and system for analyzing respiratory tract sounds in an individual. A plurality of N transducers are fixed over the thorax. The ith transducer is fixed at a location $x_i$, and generates a signal $P(x_i,t)$ indicative of pressure waves at the location $x_i$, for i=1 to N. A processor receives the signals $P(x_i,t)$ and determines an average acoustic energy $\tilde{P}(x,t_1,t_2)$ at at least one position x over a time interval where $\tilde{P}_{is}$ determined in an algorithm involving at least one of the signals $P(x_i,t)$.

31 Claims, 14 Drawing Sheets

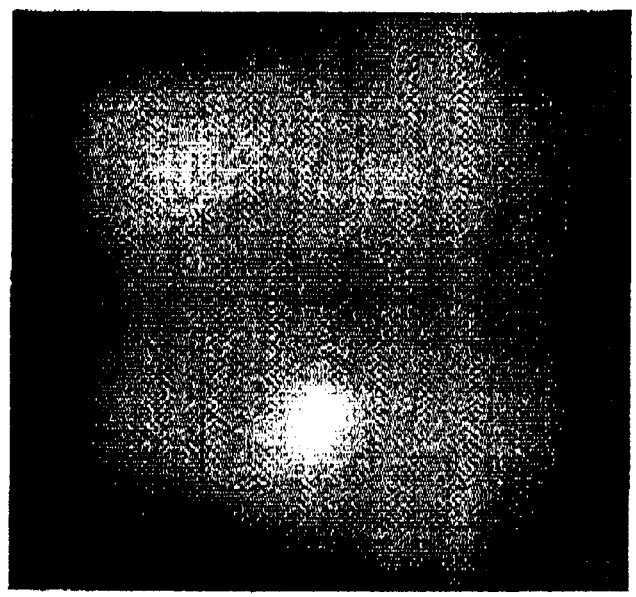
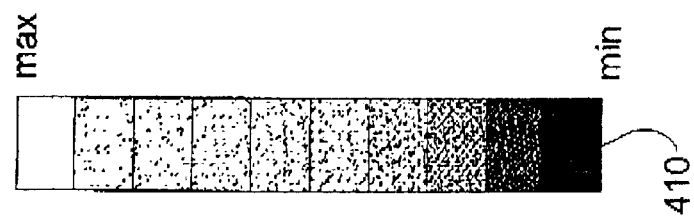
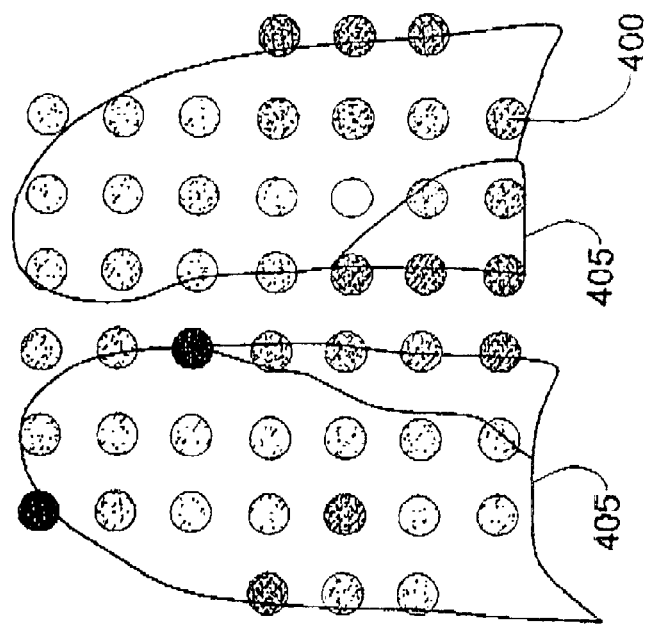
FIG. 4B
FIG. 4A

120(4), 2001) disclose a system in which M microphones are

METHOD AND SYSTEM FOR ANALYZING RESPIRATORY TRACT SOUNDS

This application is a continuation-in-part of Application No. 10/041,494 filed on Jan. 10, 2002 now abandoned, the entire contents of which are hereby incorporated by reference.

FIELD OF THE INVENTION

This invention relates to medical devices and methods, and more particularly to such devices and methods for analyzing body sounds.

BACKGROUND OF THE INVENTION

Body sounds are routinely used by physicians in the diagnosis of various disorders. A physician may place a stethoscope on a person's chest or back and monitor the patient's breathing in order to detect adventitious (i.e. abnormal or unexpected) lung sounds. The identification and classification of adventitious lung sounds often provides important information about pulmonary abnormalities.

It is also known to fix one or more microphones onto a subject's chest or back and to record lung sounds. U.S. Pat. No. 6,139,505 discloses a system in which a plurality of microphones are placed around a patient's chest. The recordings of the microphones during inhalation and expiration are displayed on a screen, or printed on paper. The recordings are then visually examined by a physician in order to detect a pulmonary disorder in the patent. Kompis et al. (Chest, 120(4), 2001) disclose a system in which M microphones are placed on a patient's chest, and lung sounds are recorded. The recordings generate M linear equations that are solved using a least-squares fit. The solution of the system is used to determine the location in the lungs of the source of a sound detected in the recordings.

SUMMARY OF THE INVENTION

In the following description and set of claims, two explicitly described, calculable, or measurable variables are considered equivalent to each other when the two variables are proportional to one another.

The present invention provides, in one of its embodiments, a system and method for recording and analyzing respiratory tract sounds produced in the respiratory tract. The system includes a plurality of N transducers (microphones) configured to be attached to an essentially planar region R of the individual's back or chest over the individual's thorax. Positions in the region R are indicated by two-dimensional position vectors $x=(x^1,x^2)$ in a two-dimensional coordinate system defined in the planar region R. The ith transducer, for $i=1$ to N, is fixed at a position $x_i$ in the region R and generates a signal, denoted herein by $P(x_i,t)$, indicative of pressure waves in the body arriving at $x_i$.

The transducers are typically embedded in a matrix that permits to affix them easily onto the individual's skin. Such a matrix may typically be in the form of a vest or garment for easily placing over the individual's thorax. As may be appreciated, different matrices may be used for differently sized individuals, for different ages, sexes, etc.

The N signals $P(x_i, t)$ are processed by signal processing circuitry. In accordance with the invention, the processing involves determining from the N signals an average acoustic energy, denoted herein by $\tilde{P}(x,t_1,t_2)$, at least one position x in the region R over a time interval from $t_1$ to $t_2$. The term "acoustic energy" at a location is used herein to refer to a parameter indicative of or approximating the product of the pressure and the mass propagation velocity at that location.

In one embodiment, an average acoustic energy over a time interval from $t_1$ to $t_2$ is obtained at a position of one of the microphones using the algebraic expression:

$$\tilde{P}(x_i, t_1, t_2) = \int_{t_1}^{t_2} P^2(x_i, t)dt \quad (1)$$

where $x_i$ is the position of the microphone.

In a more preferred embodiment, an average acoustic energy $\tilde{P}(x_i, t_1, t_2)$ over a time interval from $t_1$ to $t_2$ is obtained at a plurality of positions $x_i$ of the microphones, for example using Equation (1), and then calculating $\tilde{P}(x, t_1, t_2)$ at other locations x by interpolation of the $\tilde{P}(x_i,t_1,t_2)$ using any known interpolation method.

In a most preferred embodiment, the interpolation is performed to obtain an average acoustic energy $\tilde{P}(x,t_1,t_2)$ at a position $x=(x^1,x^2)$ in the surface R using the algebraic expression:

$$\tilde{P}(x, t_1, t_2) = \sum_{i=1}^{N} \tilde{P}(x_i, t_1, t_2)g(x, x_i, \sigma) \quad (2)$$

where $g(x,x_i,\sigma)$ is a kernel satisfying $$\nabla^2 g = \frac{\partial g}{\partial \sigma} \quad (3)$$

$$\sum_{i=1}^{N} g(x, x_i, \sigma) \text{ is approximately equal to 1} \quad (4)$$

and where $x_i=(x_i^1,x_i^2)$ is the position of the ith microphone and $\sigma$ is a selectable parameter.

For example, the kernel $$g(x, x_i, \sigma) = \text{Exp}-\left(\frac{(x^1 - x_i^1\sqrt{\sigma})^2}{2\sigma}\right) \cdot \text{Exp}-\left(\frac{(x^2 - x_i^2\sqrt{\sigma})^2}{2\sigma}\right) \quad (5)$$

may be used.

The system may optionally contain a display device for displaying the function $\tilde{P}$. The function $\tilde{P}$ may be displayed on the display, for example using a gray level scale, as demonstrated in the examples below. A two dimensional graphical representation of the function $\tilde{P}$ produces an image of the body region that may be analyzed for the detection of a disorder in the body region similar to the analysis of images obtained by other imaging methods such as X-ray or ultrasound imaging.

A region or regions in a displayed image that are suspected of including a pathological condition, may de identified in the image, and this may be in a number of ways, for example, by different colors, by different patterns, by way of a written text, and many other ways. The term "pathological condition" refers to any deviation from the normal, healthy condition of the respiratory tract. This includes infection, inflammation, tumor, pleural effusion, pneumonia, narrowing of the airways, and other space containing lesions in the respiratory tract, etc.

Additionally, a time interval can be divided into a plurality of sub intervals, and an average acoustic energy $\tilde{P}$ determined over the region R for two or more of the sub intervals. An image of $\tilde{P}$ for each of these sub intervals may then be determined and displayed sequentially on the display device. This generates a movie showing dynamic changes occurring in the acoustic energy in the body region, over the time interval. For example, transducers may be placed on a person's chest and an average acoustic energy $\tilde{P}$ determined in accordance with the invention for a plurality of sub intervals over a breathing cycle. An image can be obtained for each of these sub intervals and displayed sequentially so as to generate a movie showing changes in the acoustic energy of the lungs over the breathing cycle.

The signals $P(x_i,t)$ may also be subjected to band pass filtering before being analyzed by the method of the invention, so that an average acoustic energy is produced for one or more frequency bands of interest. The functions may be superimposed on the display device by representing each average acoustic energy function with a different color. Since respiratory sounds known as "wheezes" and "crackles" have different characteristic frequency ranges, band pass filtering can be used to identify these respiratory sounds. A region or regions in a displayed image of wheezes or crackles may be identified in the image, for example, by a characteristic color, pattern, by way of a written text.

The present invention thus provides a system for analyzing sounds in at least portion of an individual's respiratory tract comprising:

(a) a plurality of N transducers, each transducer configured to be fixed on a surface of the individual over the thorax, the ith transducer being fixed at a location $x_i$ and generating a signal $P(x_i, t)$ indicative of pressure waves at the location $x_i$; for i=1 to N; and (b) a processor configured to receive the signals $P(x_i,t)$ and determine an average acoustic energy $\tilde{P}(x,t_1,t_2)$ at at least one position x over a time interval from a first time $t_1$ to a second time $t_2$, $\tilde{P}$ being determined in an algorithm involving at least one of the signals $P(x_i, t)$.

The present invention further provides a method for analyzing sounds in at least a portion of an individual's thorax, comprising:

(One) obtaining N signals $P(x_i,t)$ for i=1 to N, the signal $P(x_i,t)$ being indicative of pressure waves at the location $x_i$; on a surface of the body over the thorax;

(Two) determining an average acoustic energy $\tilde{P}(x,t_1,t_2)$ at at least one position x over a time interval from a first time $t_1$ to a second time $t_2$, $\tilde{P}$ determined in an algorithm involving at least one of the signals.

The present invention also provides a program storage device readable by machine, tangibly embodying a program of instructions executable by the machine to perform method steps for determining for at least one time interval, an average acoustic energy function $\tilde{P}$ using an algorithm involving at least one signal $P(xi, t)$ indicative of pressure waves at a location $x_i$ on a body surface.

The present invention still further provides a computer program product comprising a computer useable medium having computer readable program code embodied therein analyzing sounds in at least a portion of an individual's body, the computer program product comprising:

computer readable program code for causing the computer to determine, for at least one time interval, an acoustic energy function $\tilde{P}$, $\tilde{P}$ being determined in algorithm involving at least one signal $P(x_i,t)$ indicative of pressure waves at a location $x_i$ on a body surface.

BRIEF DESCRIPTION OF THE DRAWINGS

In order to understand the invention and to see how it may be carried out in practice, a preferred embodiment will now be described, by way of non-limiting example only, with reference to the accompanying drawings, in which:

FIG. 4 shows recording and analysis of signals over an expiratory phase of a respiratory cycle.

DETAILED DESCRIPTION OF THE INVENTION

Figure 1:
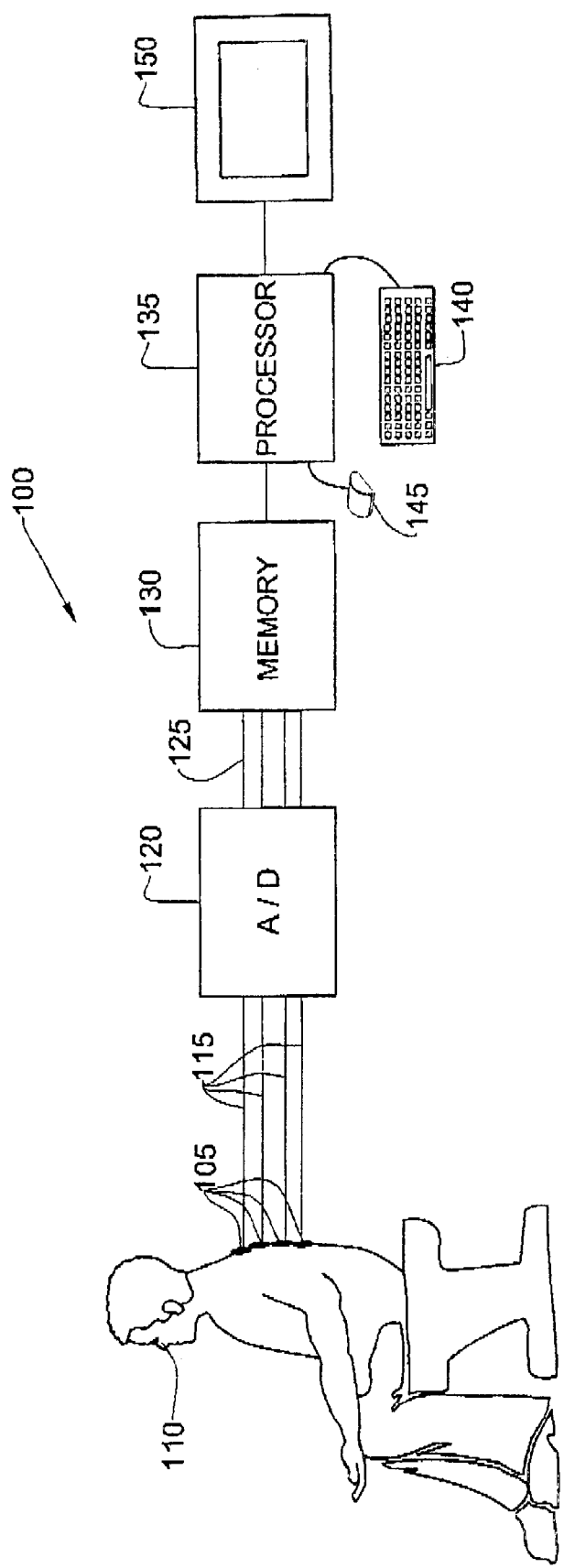
FIG. 1 shows a system for obtaining an analyzing body sound in accordance with one embodiment of the invention.

FIG. 1 shows a system generally indicated by 100 for analyzing body sounds in a three-dimensional region of an individual's body in accordance with one embodiment of the invention. A plurality of N sound transducers 105, of which four are shown, are applied to a planar region of the chest or back skin of individual 110. The transducers 105 may be applied to the subject by any means known in the art, for example using an adhesive, suction, or fastening straps. Each transducer 105 produces an analog voltage signal 115 indicative of pressure waves arriving to the transducer. The analog signals 115 are digitized by a multichannel analog to digital converter 120. The digital data signals $P(x_i,t)$ 125, represent the pressure wave at the location $x_i$ of the ith transducer (i=1 to N) at time t. The data signals 125 are input to a memory 130. Data input to the memory 130 are accessed by a processor 135 configured to process the data signals 125. The signals 125 may be denoised by filtering components having frequencies outside of the range of body sounds in the body region, for example, vibrations due to movement of the individual. Each signal 125 may also be subject to band pass filtering so that only components in the signal within a range of interest are analyzed.

An input device such as a computer keyboard 140 or mouse 145 is used to input relevant information relating to the examination such as personal details of the individual 110. The input device 140 may also be used to input values of the times $t_1$ and $t_2$. Alternatively, the times $t_1$ and $t_2$ may be determined automatically in a respiratory phase analysis of the signals $P(x_i,t)$ performed by the processor 135. The processor 135 determines an average acoustic energy $\tilde{P}(x,t_1,t_2)$ over the time interval from $t_1$ to $t_2$ at least one locations $^x$ in the region R in a calculation involving at least one of the signals $P(x_i,t)$.

The average acoustic energies are stored in the memory 130 and may be displayed on a display device 150 such as a CRT screen for diagnosis by a physician.

The processor 135 may also perform an automatic differential diagnosis by comparing the function $\tilde{P}$ to functions stored in the memory and known to be indicative of various disorders in the body region.

Figure 2:
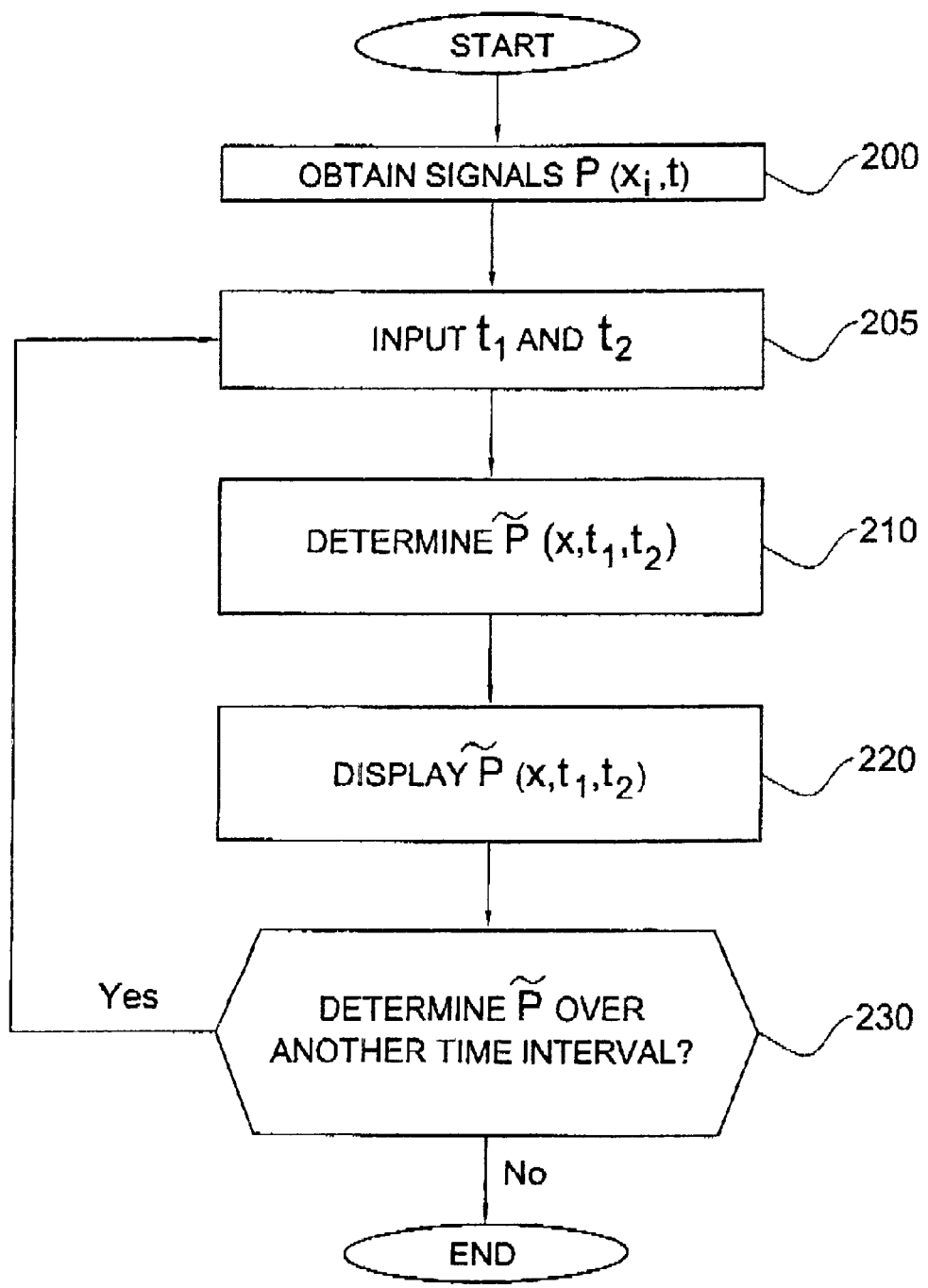
FIG. 2 shows a flow chart for carrying out a method of obtaining analyzing body sounds in accordance with one embodiment of the invention.

FIG. 2 shows a flow chart diagram for carrying out the method of the invention in accordance with one embodiment. In step 200 the signals $P(x_i,t)$ are obtained from N transducers placed at predetermined locations $x_i$ for i from 1 to N in a region R on the body surface. In step 205 values of $t_1$ and $t_2$ are either input to the processor 135 using the input devices 140 or 145, or are determined by the processor. In step 210, an average acoustic energy $\tilde{P}(x,t_1,t_2)$ is determined at least one location x in the region R over the time interval $t_1$ to $t_2$. In step 220 the average acoustic energy is displayed on the display 150 for at least one value of x. In step 230, it is determined whether a function $\tilde{P}$ is to be determined over another time interval. If yes, the process returns to step 205. If not, the process terminates.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

EXAMPLES

The system and method of the invention were used to analyze lower respiratory tract sounds in an individual.

Figure 3B:
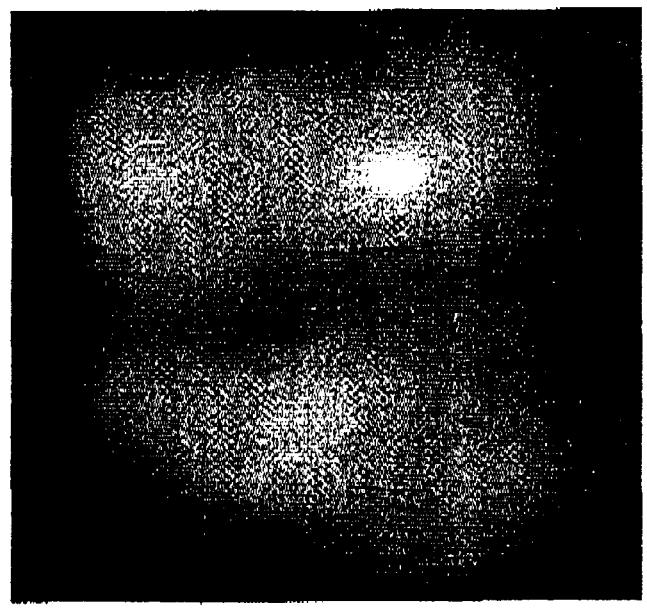
FIG. 3 shows recording and analysis of signals over an inspiratory phase of a respiratory cycle.
Figure 3A:
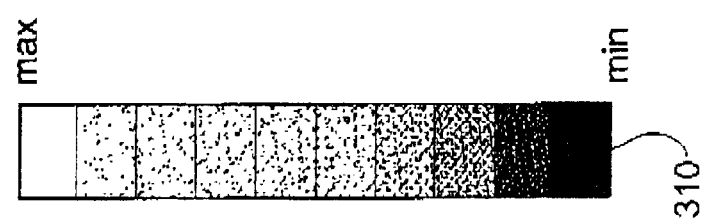
Figure 3A:
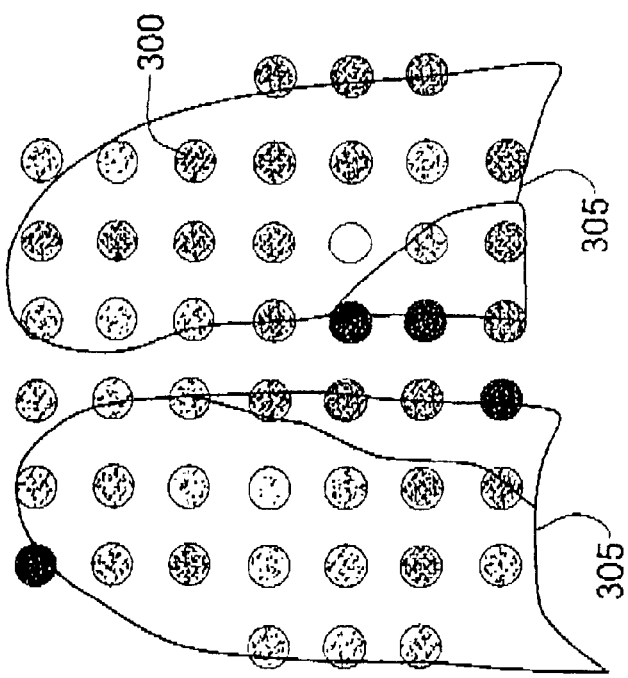

FIG. 3 shows recording and analysis of signals over an inspiratory phase of a respiratory cycle in an individual. A two-dimensional coordinate system was defined on the individual's back. As shown in FIG. 3a, 48 transducers were placed on the individual's back over the lungs at the locations indicated by the circles 300. The curves 305 show the presumed contours of the lungs. As can be seen, the transducers were arranged in a regular orthogonal lattice with a spacing between the transducers in the horizontal and vertical directions of 5 cm. The signals $P(x_i,t)$ were then recorded over one inspiratory phase of a breathing cycle ($t_1$ and $t_2$ are the beginning and end respectively of the inspiratory phase). Each signal was filtered using a low-pass filter having a cut-off of 150 Hz. The average value of each filtered function $P(x_i,t)$ over the inspiratory phase is indicated in FIG. 3a by means of gray level shading of each circle 300 with reference to the gray level scale 310. $\tilde{P}(x,t_1,t_2)$ was obtained using Equations (1) and (2) above with the kernel g of Equation (5) with σ=36 pixels. FIG. 3b shows a 512 pixel×512 pixel graphical representation of the function $\tilde{P}(x,t_1,t_2)$ over the inspiratory phase also in reference to the gray level scale 310. In the graphical representation of the function $\tilde{P}(x,t_1,t_2)$ shown in FIG. 3b, the contours of the lungs and heart are easily discernable.

FIG. 4 shows recording and analysis of signals over an expiratory phase of a respiratory cycle. As shown in FIG. 4a, 48 transducers were placed on an individual's back at the same locations $x_i$ used in FIG. 3, as indicated by the circles 400. The curves 405 show the presumed contours of the individual's lungs. The signals $P(x_i,t)$ were then recorded over one expiratory phase of a breathing cycle ($t_1$ and $t_2$ are the beginning and end respectively of the expiratory phase). Each signal was filtered using a low-pass filter having a cut-off of 150 Hz. The average value of each function $P(x_i,t)$ over the expiratory phase is indicated in FIG. 4a by means of gray level shading of each circle 400 with reference to the gray level scale 410. $\tilde{P}(x,t_1,t_2)$ was obtained using Equations (1) and (2) above. FIG. 3b shows the function $\tilde{P}(x,t_1,t_2)$ over the expiratory phase also in reference to the gray level scale 410. Comparison of FIGS. 3b and 4b shows the volume change in acoustic energy between the inspiratory and expiratory phase of the respiratory cycle.

Movies showing changes in the lungs during a respiratory cycle were obtained using the method and system of the invention. Signals 125 were obtained and divided into time segments of 0.5 sec duration. Each segment was analyzed by the method of the invention and an image was generated. The images were displayed on the display device 150 in rapid succession so as to produce a movie of the respiratory tract over the respiratory cycle.

Figure 5A:
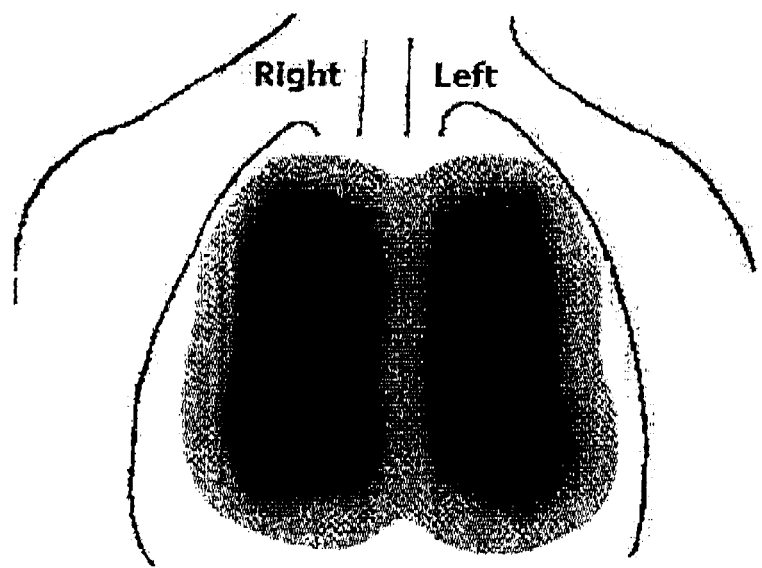
FIG. 5a shows an image obtained on a healthy individual in accordance with the invention.
Figure 5B:
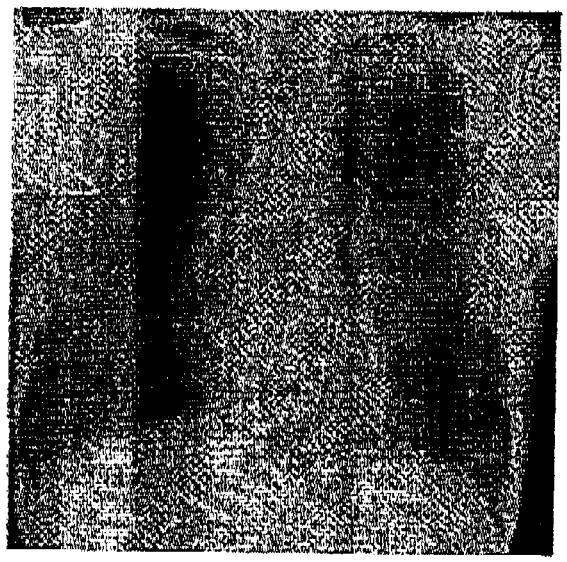
FIG. 5b shows a chest X-ray of the same individual.
Figure 6A:
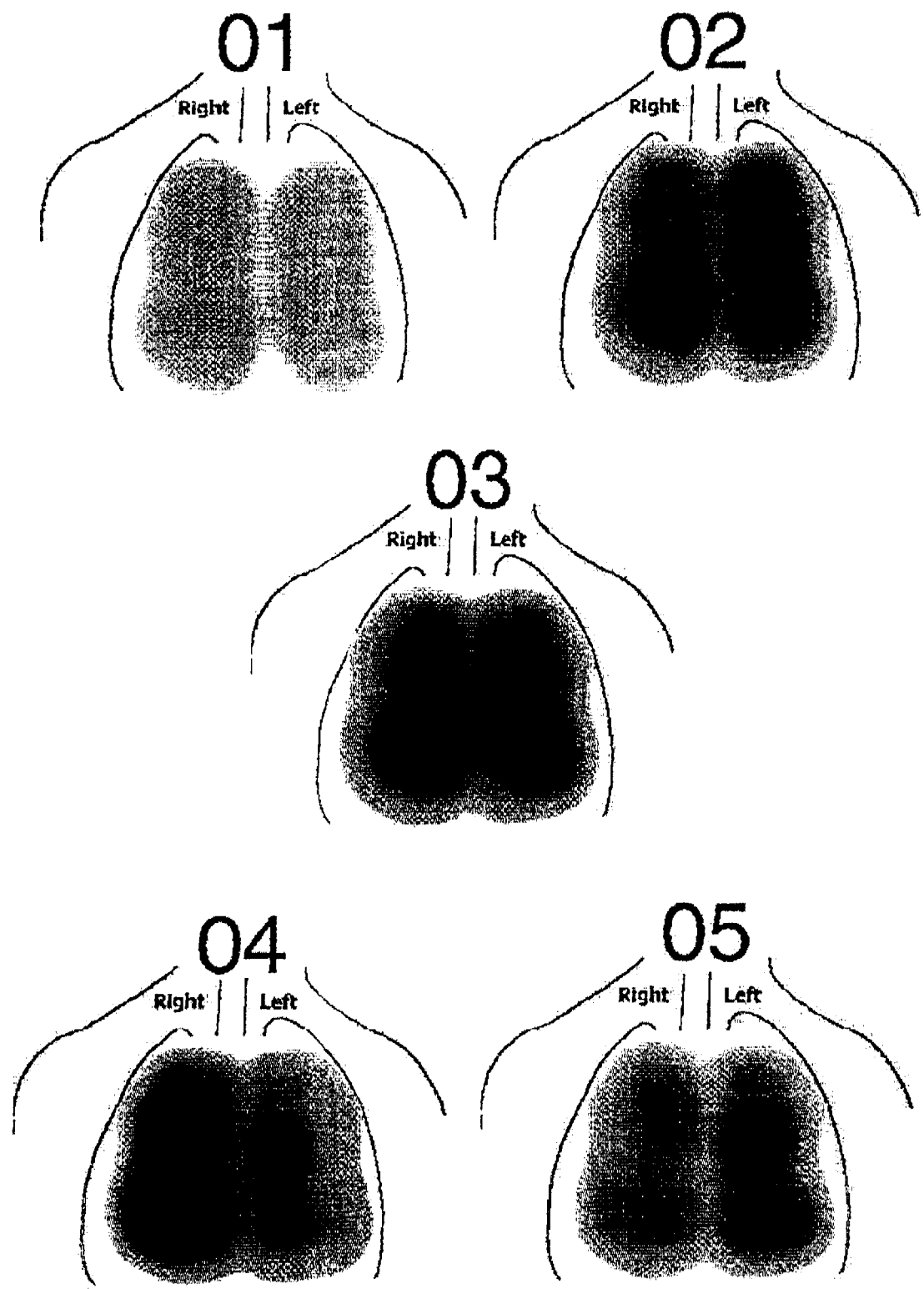
FIG. 6 shows successive frames from a movie of the respiratory tract of a healthy individual.
Figure 6B:
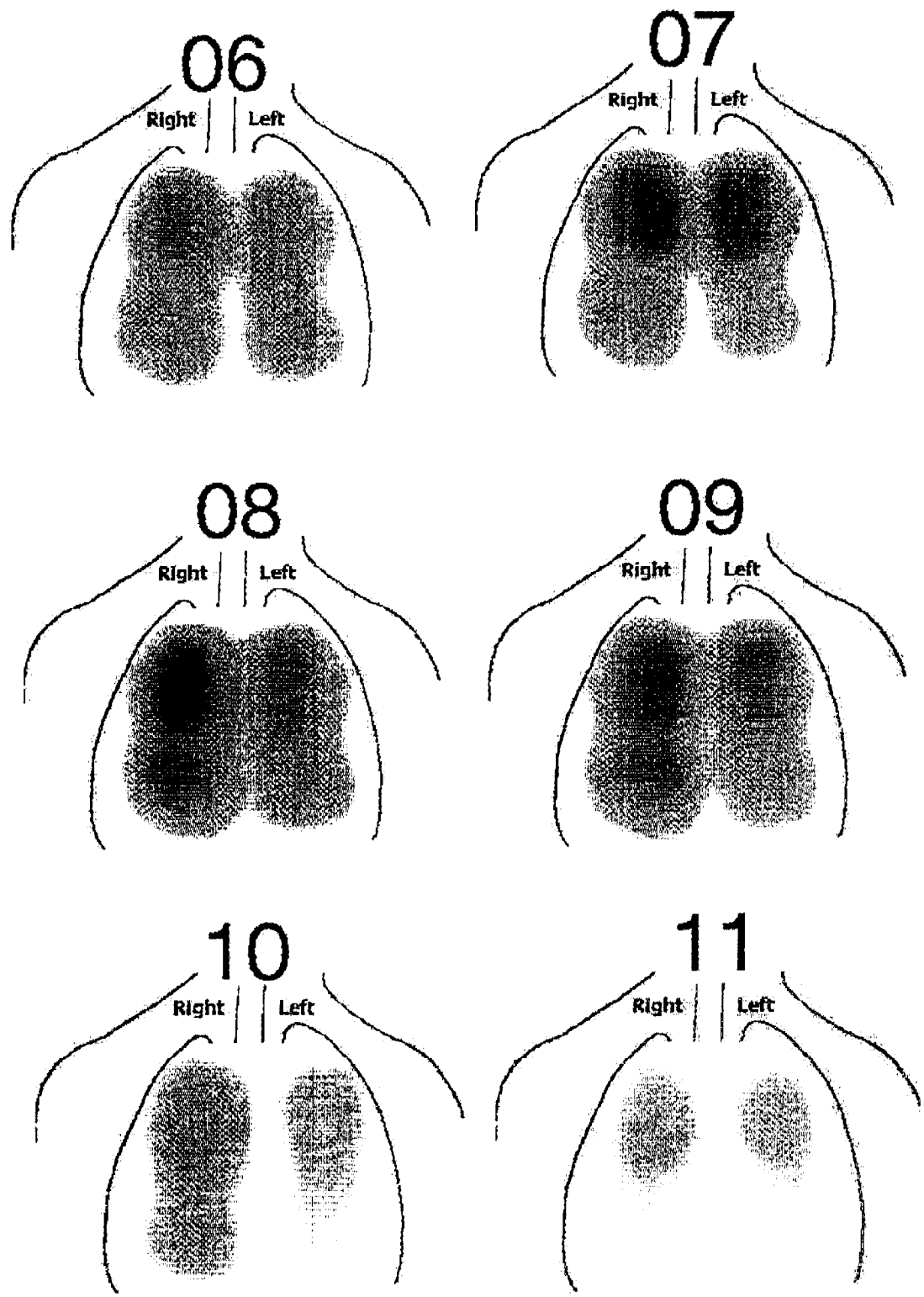

FIG. 5a shows an image of the respiratory tract of a healthy individual obtained over an entire respiratory cycle in accordance with the invention, and FIG. 5b shows a chest X-ray of the same individual. FIG. 6 shows 11 successive images obtained over successive 0.4 sec time intervals during a respiratory cycle of the individual. Each frame represents the processing of the recorded signals over a time interval of 0.4 sec. Frames 01 to 05 (obtained at times 0.0 to 1.6 sec) were obtained during the inspiratory phase of the respiratory cycle, while frames 06 to 11 (obtained at times 1.8 to 3.6 sec) were obtained during the expiratory phase. The sequence of images shown in FIG. 6 can be displayed in succession on a display device so as to create a movie of the respiratory tract over a respiratory cycle. The sequence of images shown in FIG. 6 shows complete filling and emptying of the lungs during the respiratory cycle, as would be expected in a healthy individual not having any space-filling lesions.

Figure 7A:
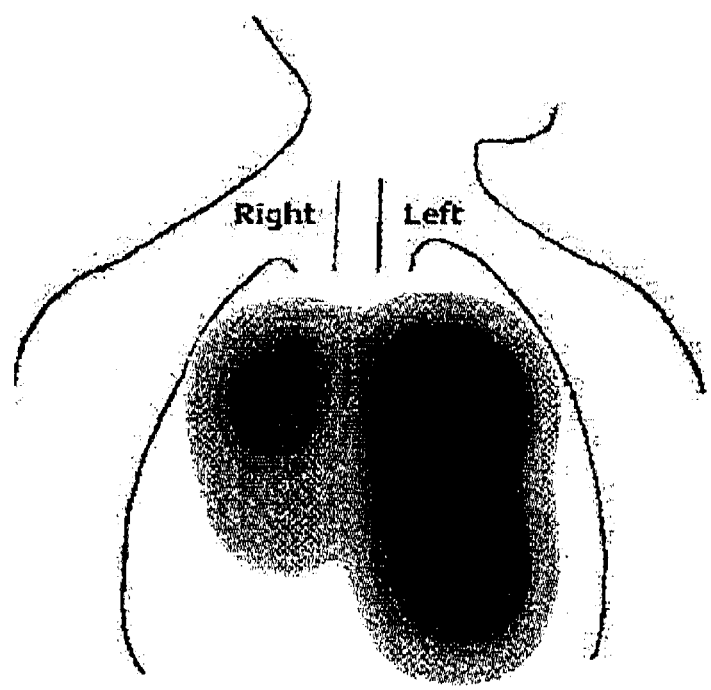
FIG. 7a shows an image obtained on an individual with pleural effusion in accordance with the invention.
Figure 7B:
FIG. 7b shows a chest X-ray of the same individual.
Figure 8A:
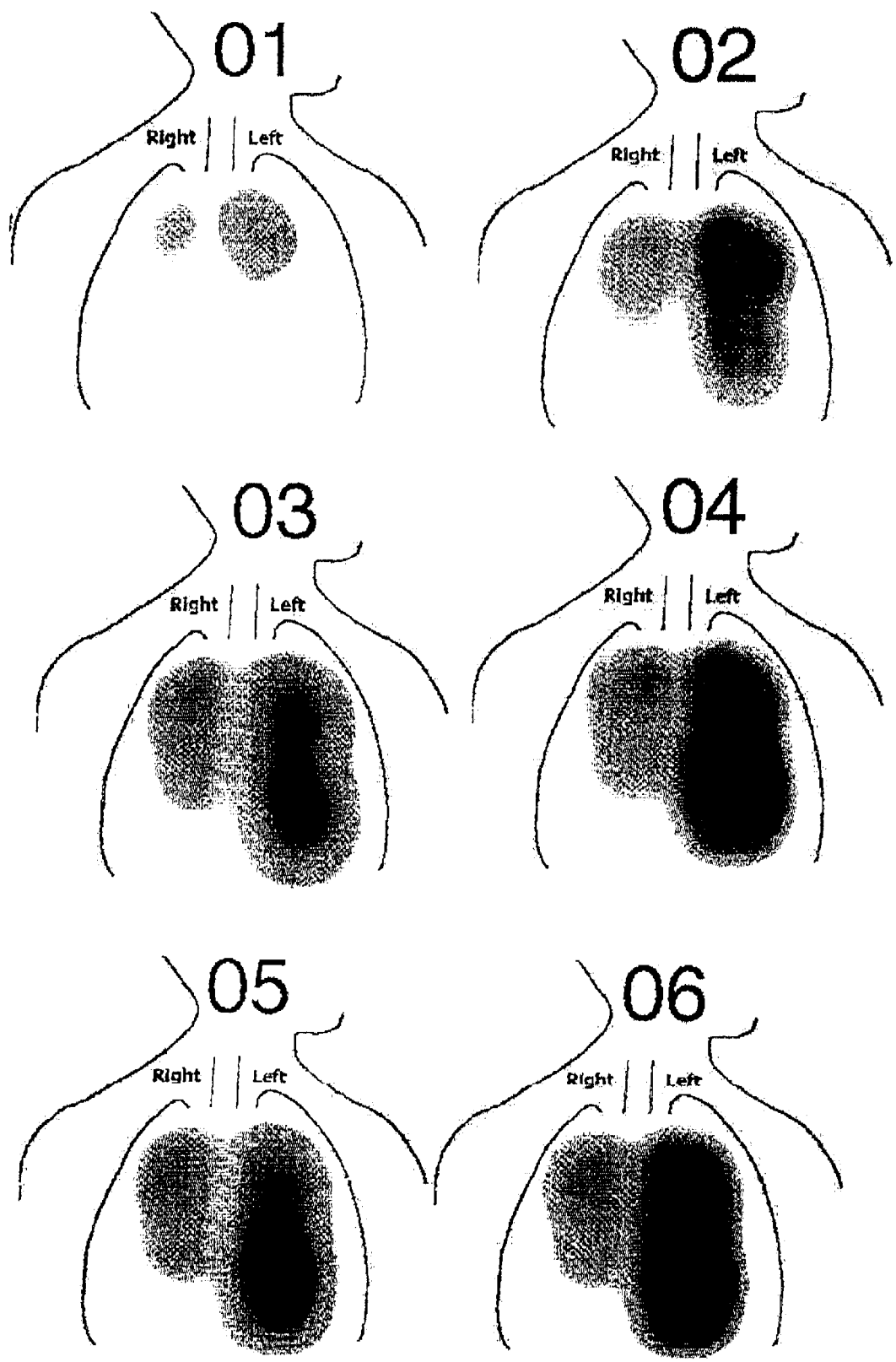
FIG. 8 shows successive frames from a movie of the respiratory tract of an individual with pleural effusion.
Figure 8B:
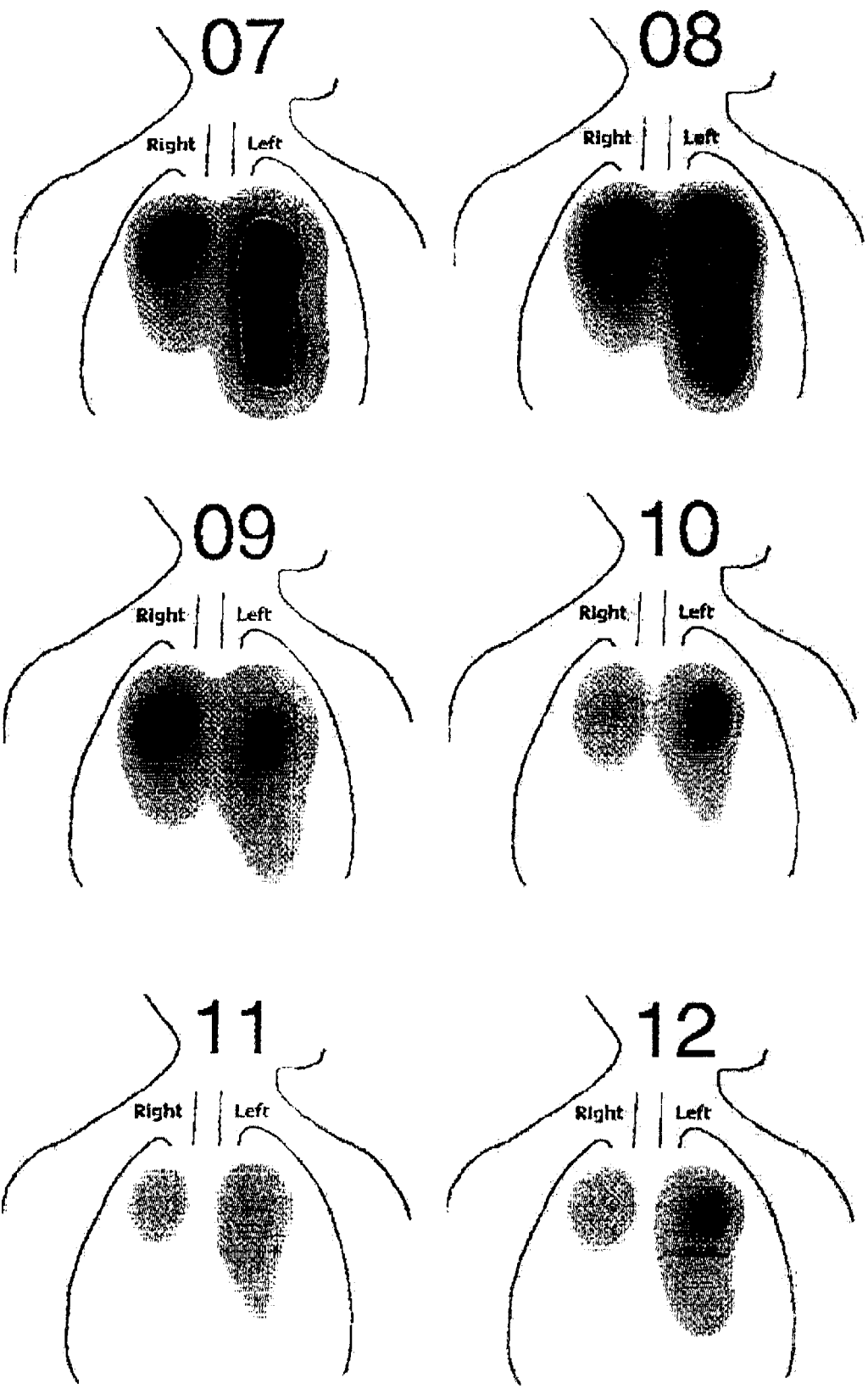
Figure 8C:
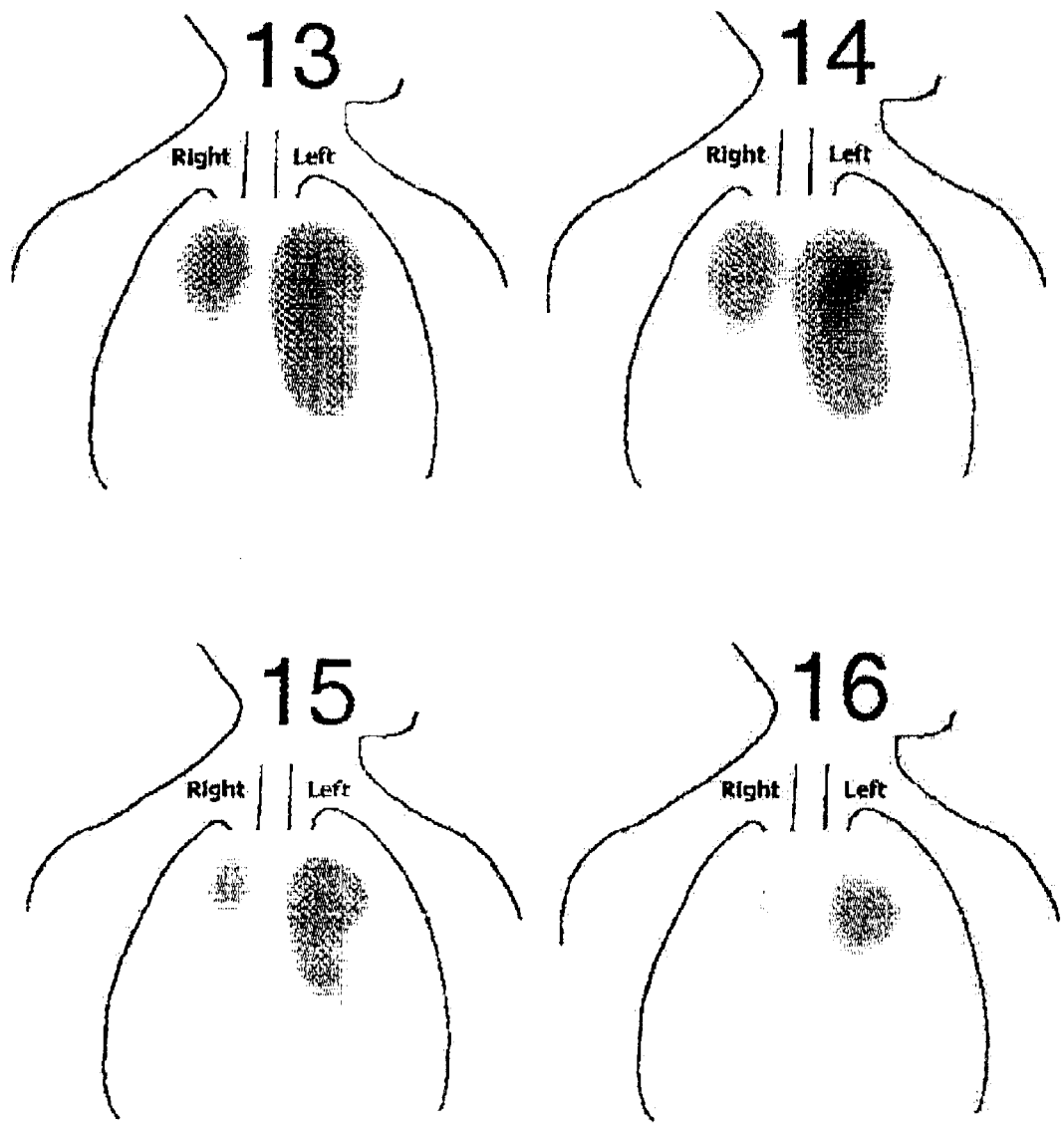

FIG. 7a shows an image of the respiratory tract of an individual with pleural effusion obtained over an entire respiratory cycle in accordance with the invention, and FIG. 7b shows a chest X-ray of the same individual. FIG. 8 shows 16 successive images obtained over successive 0.4 sec time intervals during a respiratory cycle of the individual. Each frame represents the processing of the recorded signals over a time interval of 0.4 sec. Frames 01 to 06 (obtained at times 0.0 to 2.0 sec) were obtained during the inspiratory phase of the respiratory cycle, while frames 07 to 16 (obtained at times 2.4 to 4.0 sec) were obtained during the expiratory phase. The sequence of images shown in FIG. 8 can be displayed in succession on a display device so as to create a movie of the respiratory tract over a respiratory cycle. In the sequence of images shown in FIG. 8, lung tissue in the lower right lobe is not visualized indicating the absence of air flow in the lower right lung, as would be expected in an individual having a space-filling lesion as occurs in pleural effusion. Airflow in the upper portion of the right lung is also observed to be impaired.

Figure 9A:
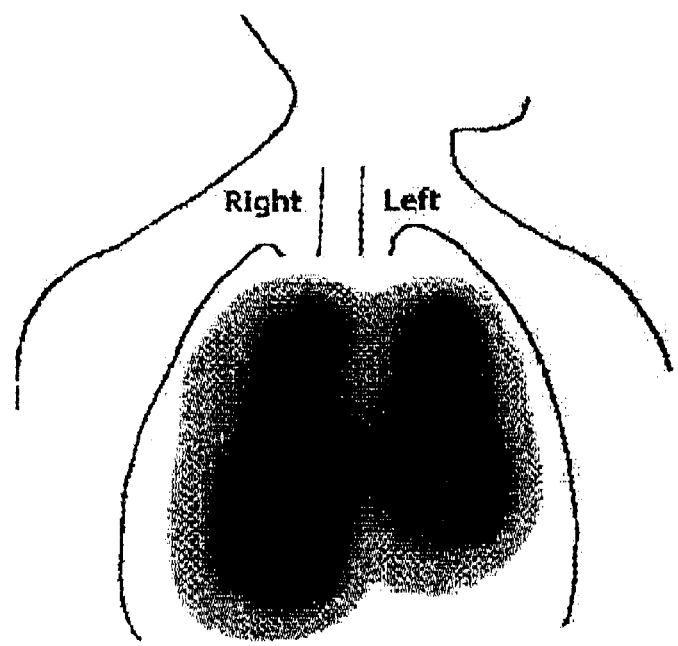
FIG. 9a shows an image obtained on an individual with pneumonia in accordance with the invention.
Figure 9B:
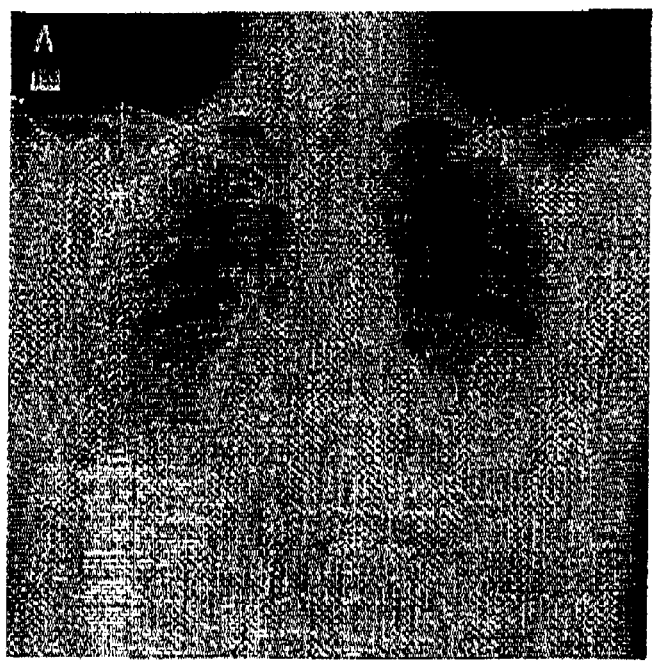
FIG. 9b shows a chest X-ray of the same individual.
Figure 10A:
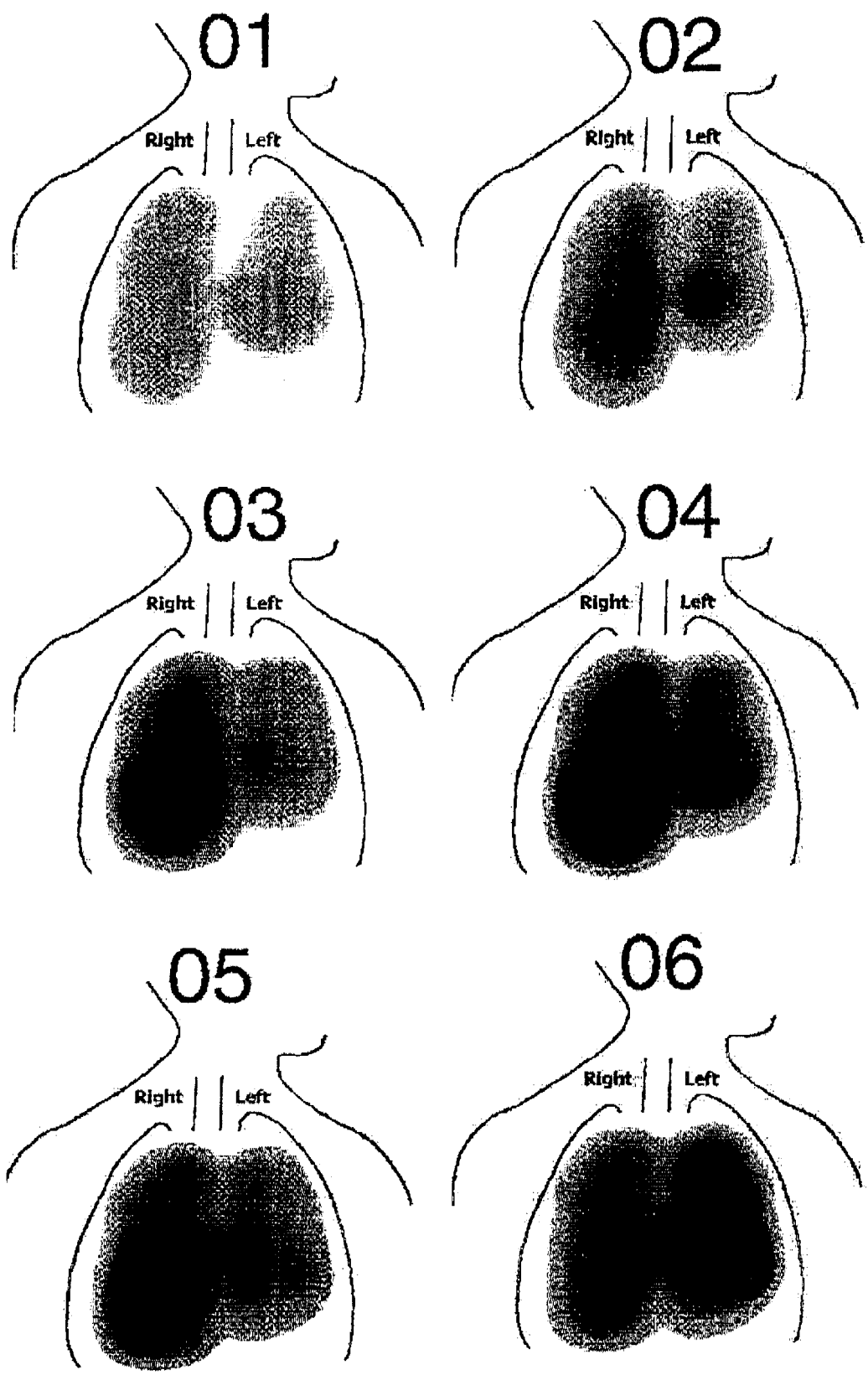
FIG. 10 shows successive frames from a movie of the respiratory tract of an individual with pleural effusion.
Figure 10B:
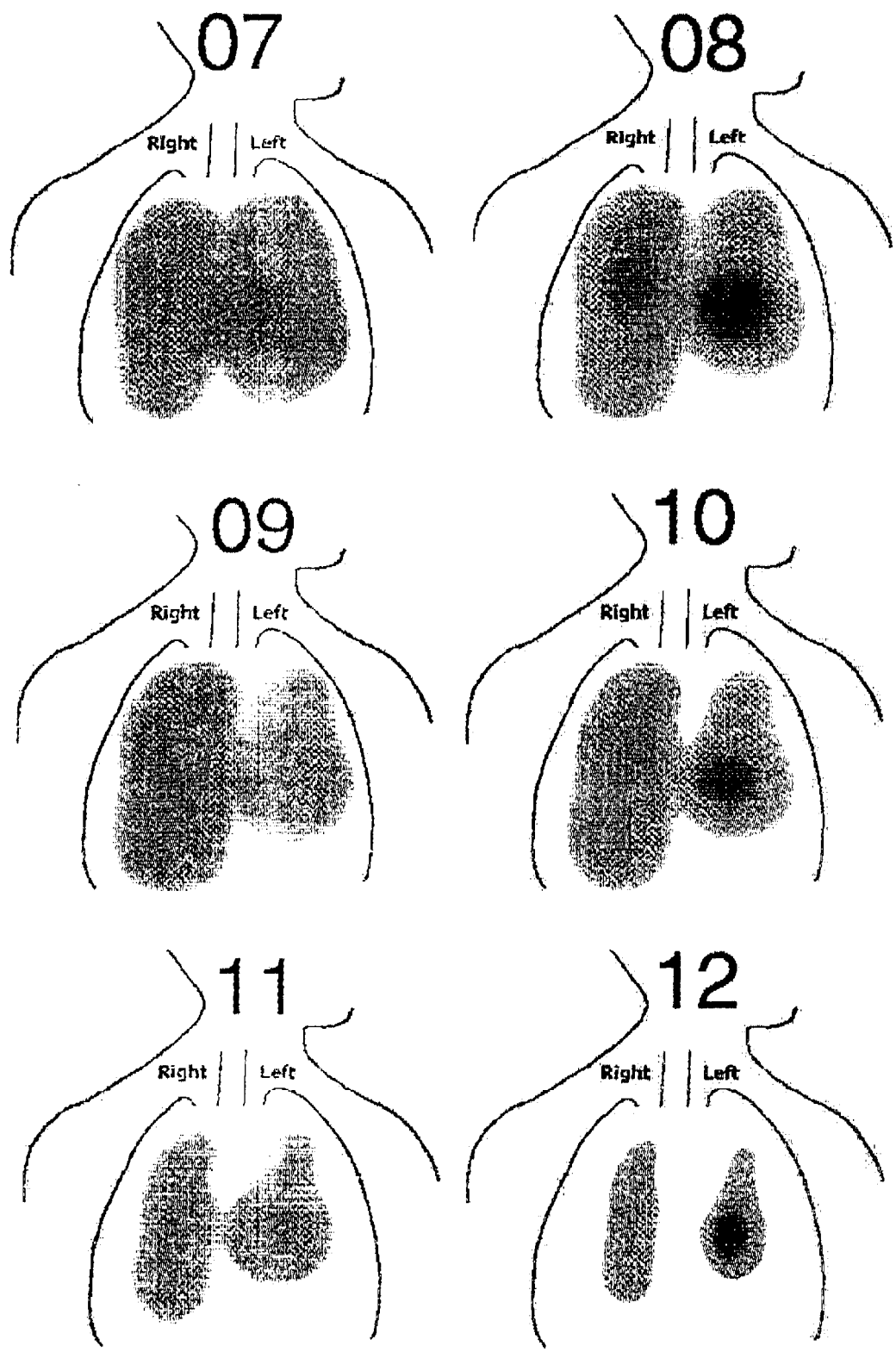

FIG. 9a shows an image of the respiratory tract of an individual with pneumonia obtained over an entire respiratory cycle in accordance with the invention, and FIG. 9b shows a chest X-ray of the same individual. FIG. 10 shows 12 successive images obtained over successive 0.4 sec time intervals during a respiratory cycle of the individual. The sequence of images shown in FIG. 10 can be displayed in succession on a display device so as to create a movie of the respiratory tract over a respiratory cycle. Each frame represents the processing of the recorded signals over a time interval of 0.4 sec. Frames 01 to 06 (obtained at times 0.0 to 2.0 sec) were obtained during the inspiratory phase of the respiratory cycle, while frames 07 to 16 (obtained at times 2.4 to 4.0 sec) were obtained during the expiratory phase. In the sequence of images shown in FIG. 10, lung tissue in the lower left lobe is not visualized indicating the absence of air flow in the lower left lung, as would be expected in an individual having a space-filling lesion as occurs in pneumonia. Airflow in the upper portion of the left lung is observed to be normal.

What is claimed is:

1. A system for analyzing sounds in at least a portion of an individual's respiratory tract comprising:

(a) a plurality of N transducers, each transducer configured to be fixed on a surface of the individual over the thorax, the ith transducer being fixed at a location $x_i$ and generating a signal $P(x_i, t)$ indicative of pressure waves at the location $x_i$; for i=1 to N; and (b) a processor configured to receive the signals $P(x_i, t)$ and determine an average acoustic energy $\tilde{P}(x, t_1, t_2)$ at at least one position x over a time interval from a first time $t_1$ to a second time $t_2$, $\tilde{P}$ being determined in an algorithm involving at least one of the signals $P(x_i, t)$.

2. The system according to claim 1 further comprising a two-dimensional display device.

3. The system according to claim 2 wherein the processor is further configured to display a representation of the function $\tilde{P}$ on the display device.

4. The system according to claim 1 wherein the processor is further configured to compare the average acoustic energy $\tilde{P}$ to one or more predetermined functions $\tilde{F}$ and determine a function $\tilde{F}_0$ from among the functions $\tilde{F}$ most similar to $\tilde{P}$.

5. The system according to claim 4 wherein the processor is further configured to make a diagnosis based upon the determined function.

6. The system according to claim 1 wherein the average acoustic energy $\tilde{P}$ over a time interval from $t_1$ to $t_2$ is determined at a location $x_i$ of a transducer using the algebraic expression:

$$\tilde{P}(x_i, t_1, t_2) = \int_{t_1}^{t_2} P^2(x_i, t)\, dt.$$

7. The system according to claim 1 wherein the function $\tilde{P}$ is determined at one or more locations x in an algorithm comprising:

(One) determining an average acoustic energy $\tilde{P}(x_i, t_1, t_2)$ over a time interval from $t_1$ to $t_2$ at a plurality of locations $x_i$ of transducers; and (Two) determining an average acoustic energy $\tilde{P}(x, t_1, t_2)$ at at least one location $x$ by interpolation of the determined $\tilde{P}(x, t_1, t_2)$.

8. The system according to claim 7 wherein an average acoustic energy $\tilde{P}(x_i, t_1, t_2)$ is determined over a time interval from $t_1$ to $t_2$ at a plurality of locations $x_i$ of transducers using the algebraic expression:

$$\tilde{P}(x_i, t_1, t_2) = \int_{t_2}^{t_2} P^2(x_i, t)\, dt.$$

9. The system according to claim 7 wherein an average acoustic energy is determined at at least one location x by interpolation of the determined $\tilde{P}(x_i, t_1, t_2)$ using the algebraic expression:

$$\tilde{P}(x, t_1, t_2) = \sum_{i=1}^{N} \tilde{P}(x_i, t_1, t_2) g(x, x_i, \sigma) \quad (2)$$

where $g(x, x_i, \sigma)$ is a kernel satisfying $$\nabla^2 g = \frac{\partial g}{\partial \sigma} \quad (3)$$

$$\sum_{i=1}^{N} g(x, x_i, \sigma) \text{ is approximately equal to } 1. \quad (4)$$

10. The system according to claim 9 wherein $g(x,x_i,\sigma)$ is the kernel $g(x,x_i,\sigma)=$ $$\mathrm{Exp}-\left(\frac{(x^1 - x_i^1 \sqrt{\sigma})^2}{2\sigma}\right) \cdot \mathrm{Exp}-\left(\frac{(x^2 - x_i^2 \sqrt{\sigma})^2}{2\sigma}\right). \quad (5)$$

11. The system according to claim 1 wherein the processor is configured to determine an average acoustic energy over a plurality of successive time intervals, each average acoustic energy being determined using an algorithm involving at least one of the signals $P(x_i, t)$.

12. The system according to claim 11 wherein the processor is configured to sequentially display on a display device a representation of each determined average acoustic energy.

13. The system according to claim 1 wherein the processor is configured to:

for each of one or more frequency bands,
     subject the signals $P(x_i, t)$ to band pass filtering in the frequency band; and
   determine an average acoustic energy function for the frequency band based upon at least one of the filtered signals.

14. The system according to claim 13 wherein the processor is configured to display one or more of the average acoustic energy functions determined for a frequency band on a display device.

15. A method for analyzing sounds in at least a portion of an individual's thorax, comprising:

(One) obtaining N signals $P(x_i, t)$ for i=1 to N, the signal $P(x_i, t)$ being indicative of pressure waves at the location $x_i$; on a surface of the body over the thorax;

(Two) determining an average acoustic energy $\tilde{P}(x, t_1, t_2)$ at at least one position x over a time interval from a first time $t_1$ to a second time $t_2$, $\tilde{P}$ determined in an algorithm involving at least one of the signals.

16. The method according to claim 15 further comprising displaying a representation of $\tilde{P}$ on a two-dimensional surface.

17. An image of a two-dimensional representation of $\tilde{P}$ produced by the method of claim 16.

18. The method according to claim 15 wherein further comprising making a diagnosis based upon the determined average acoustic energy.

19. The method according to claim 15 wherein the average acoustic energy over a time interval from $t_1$ to $t_2$ is determined at a location $x_i$ of a transducer using the algebraic expression:

$$\tilde{P}(x_i, t_1, t_2) = \int_{t_1}^{t_2} P^2(x_i, t) dt.$$

20. The method according to claim 15 wherein the function $\tilde{P}$ is determined at one or more locations x in an algorithm comprising:

(One) determining an average acoustic energy $\tilde{P}(x_i,t_1,t_2)$ over a time interval from $t_1$ to $t_2$ at a plurality of locations $x_i$ of transducers; and (Two) determining an average acoustic energy $\tilde{P}(x,t_1, t_2)$ at at least one location x by interpolation of the determined $\tilde{P}(x,t_1,t_2)$.

21. The method according to claim 20 wherein an average acoustic energy $\tilde{P}(x,t_1,t_2)$ is determined over a time interval from $t_1$ to $t_2$ a at a plurality of locations of transducers using the algebraic expression:

$$\tilde{P}(xi, t_1, t_2) = \int_{t_1}^{t_2} P^2(x_i, t) dt$$

22. The method according to claim 20 wherein an average acoustic energy is determined at at least one location x by interpolation of the determined $\tilde{P}(x,t_1,t_2)$ using the algebraic expression:

$$\tilde{P}(x, t_1, t_2) = \sum_{i=1}^{N} \tilde{P}(x_i, t_1, t_2) g(x, x_i, \sigma) \quad (2)$$

where $g(x,x_i,\sigma)$ is a kernel satisfying $$\nabla^2 g = \frac{\partial g}{\partial \sigma} \quad (3)$$

$$\sum_{i=1}^{N} g(x, x_i, \sigma) \text{ is approximately equal to 1.} \quad (4)$$

23. The method according to claim 22 wherein $g(x,x_i,\sigma)$ is the kernel $$g(x, x_i, \sigma) = \text{Exp} - \left( \frac{(x^1 - x_i^1 \sqrt{\sigma})^2}{2\sigma} \right) \cdot \text{Exp} - \left( \frac{(x^2 - x_i^2 \sqrt{\sigma})^2}{2\sigma} \right).$$

24. The method according to claim 15 further comprising comparing the average acoustic energy $\tilde{P}$ to one or more predetermined functions $\tilde{F}$ and determining a function $\tilde{F}_0$ from among the functions $\tilde{F}$ most similar to $\tilde{P}$.

25. The method according to claim 15 comprising determining an average acoustic energy over a plurality of successive time intervals, each average acoustic energy being determined using an algorithm involving at least one of the signals $P(x_i,t)$ further comprising sequentially displaying on a display device a representation of each determined average acoustic energy.

26. The method according to claim 15 further comprising, for each of one or more frequency bands:

(One) subjecting the signals $P(x_i,t)$ to band pass filtering in the frequency band; and (Two) determining an average acoustic energy function for the frequency band based upon at least one of the filtered signals.

27. The method according to claim 26 further comprising displaying on a display device one or more of the acoustic energy functions determined for a frequency band.

28. The method according to claim 15, further comprising diagnosing a respiratory tract disorder.

29. The method according to claim 28 wherein the disorder is selected from the group comprising at least pleural effusion and pneumonia.

30. A program storage device readable by machine, tangibly embodying a program of instructions executable by the machine to perform method steps comprising determining for at least one time interval, an average acoustic energy function $\tilde{P}$ using an algorithm involving at least one signal $P(x_i,t)$ indicative of pressure waves at a location $x_i$ on a body surface.

31. A computer program product comprising a computer useable medium having computer readable program code embodied therein analyzing sounds in at least a portion of an individual's body, the computer program product comprising:

computer readable program code for causing the computer to determine, for at least one time interval, an acoustic energy function $\tilde{P}$, $\tilde{P}$ being determined in algorithm involving at least one signal $P(x_i,t)$ indicative of pressure waves at a location $x_i$ on a body surface.

* * * * *